US00PP18658P3

(12) United States Plant Patent
Fear et al.

(10) Patent No.: US PP18,658 P3
(45) Date of Patent: Mar. 25, 2008

(54) RASPBERRY PLANT NAMED 'DRISCOLL PACIFICA'

(50) Latin Name: *Rubus idaeus*
Varietal Denomination: Rubus

(75) Inventors: Carlos Fear, Aptos, CA (US); Rick Harrison, Aptos, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 122 days.

(21) Appl. No.: 11/327,134

(22) Filed: Jan. 6, 2006

(65) Prior Publication Data

US 2007/0163016 P1 Jul. 12, 2007

(51) Int. Cl.
*A01H 5/00* (2006.01)

(52) U.S. Cl. ..... Plt./204

(58) Field of Classification Search ..... Plt./204
See application file for complete search history.

*Primary Examiner*—Wendy C. Haas
*Assistant Examiner*—Georgia Helmer
(74) *Attorney, Agent, or Firm*—Jones Day

(57) ABSTRACT

The present invention relates to a new and distinct cultivar of raspberry plant named 'Driscoll Pacifica'. The new cultivar is distinguished from other raspberry cultivars by its fruit firmness, consistent large fruit size and high yield. The new cultivar is distinguished from its parent by having better flavored fruit and larger fruit.

3 Drawing Sheets

Latin name of the genus and species of the plant claimed: The variety is botanically identified as *Rubus idaeus* L. subgenus *Rubus*.

Variety denomination: The Raspberry variety denomination is 'Driscoll Pacifica'.

BACKGROUND OF THE INVENTION

This invention relates to a new cultivar of raspberry called 'Driscoll Pacifica'. The new cultivar was developed from a single seedling selected from the hybridization of the selection 'N234.1' (an unpatented variety) as the seed parent with the selection 'Q471.6' (an unpatented variety) as the pollen parent. The parents were crossed in 1996; whereafter fruit and seed were collected to produce seedlings for field planting in Carpenteria, Calif. in 1997. The new cultivar was selected from these seedlings in 1997 for its large, firm and good flavoured fruit. The new cultivar has been asexually propagated by in vitro shoot tip culture, root sucker division and root cuttings at the Cassin Ranch in Santa Cruz County, California and has been shown to maintain the desired and distinguishing characteristics after propagation over several generations.

SUMMARY OF THE INVENTION

The present invention provides a new and distinct cultivar of red raspberry plant named 'Driscoll Pacifica'. The cultivar is botanically identified as *Rubus ideaus* L. The 'Driscoll Pacifica' red raspberry plant produces a primocane crop which begins in late June-mid July and continues until late October. The floricane crop begins in early May and continues until mid July. Both the primocane and floricane yields are high relative to other comparable varieties. The fruit of 'Driscoll Pacifica' is notably quite firm and good flavor. The fruit of 'Driscoll Pacifica' separates easily from its receptacle.

BRIEF DESCRIPTION OF THE DRAWINGS

The accompanying photographs show typical specimens of the primocane fruit, leaves and shoot of the new cultivar, in color as nearly true as it is reasonably possible to make in color illustrations of these characteristics. The specimens in FIGS. 1-3 are about 11 months old.

DETAILED BOTANICAL DESCRIPTION

Figure 1:
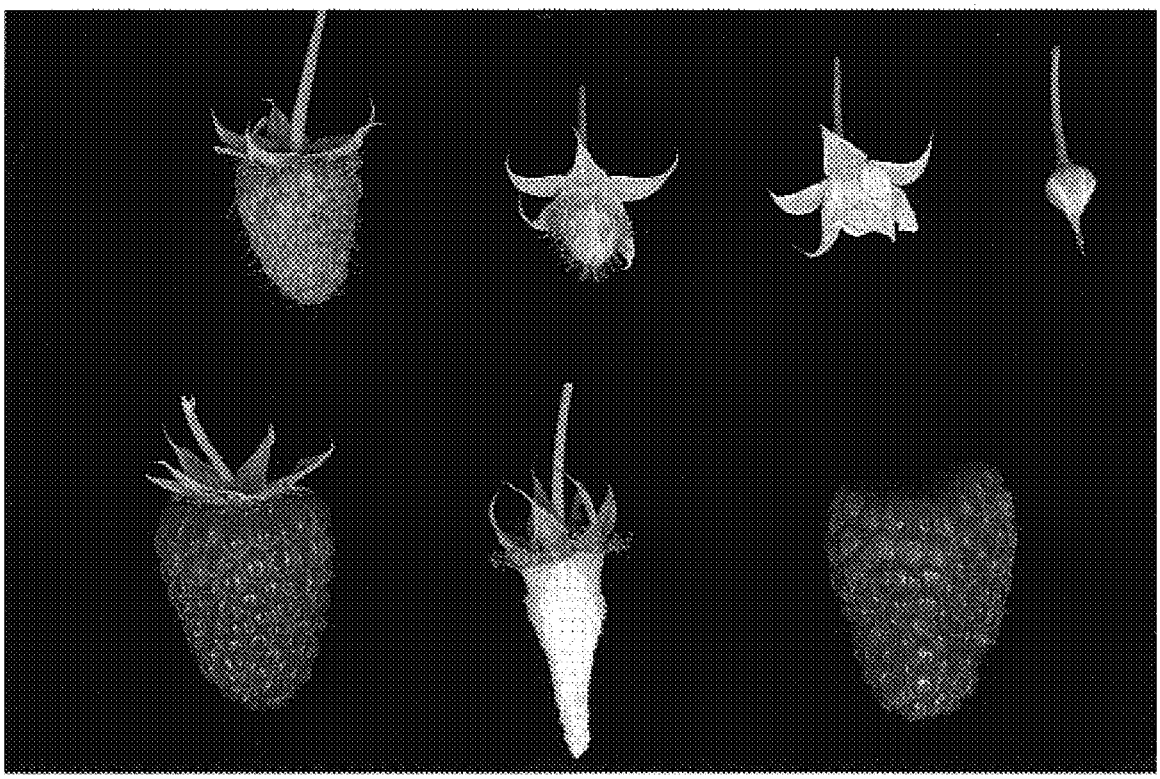
FIG. 1 is a photograph of 'Driscoll Pacifica' primocane flower and fruit in various stages of development.
Figure 2:
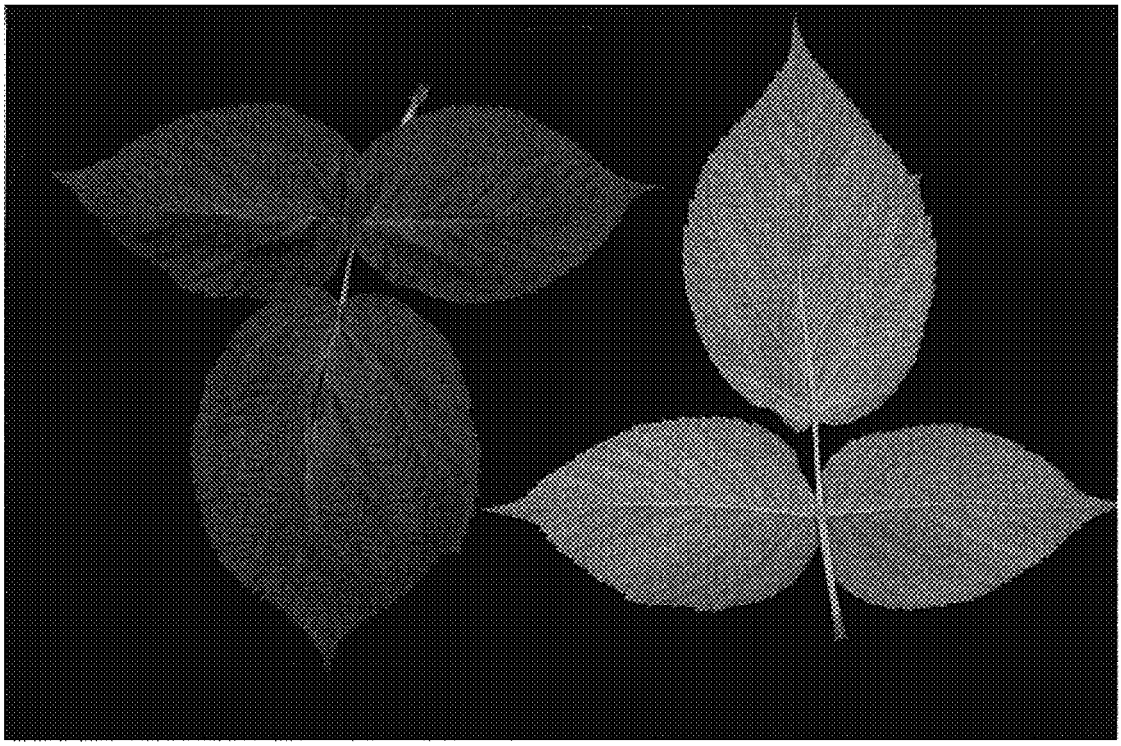
FIG. 2 is a photograph of 'Driscoll Pacifica' primocane leaves showing upper and lower leaf surfaces.
Figure 3:
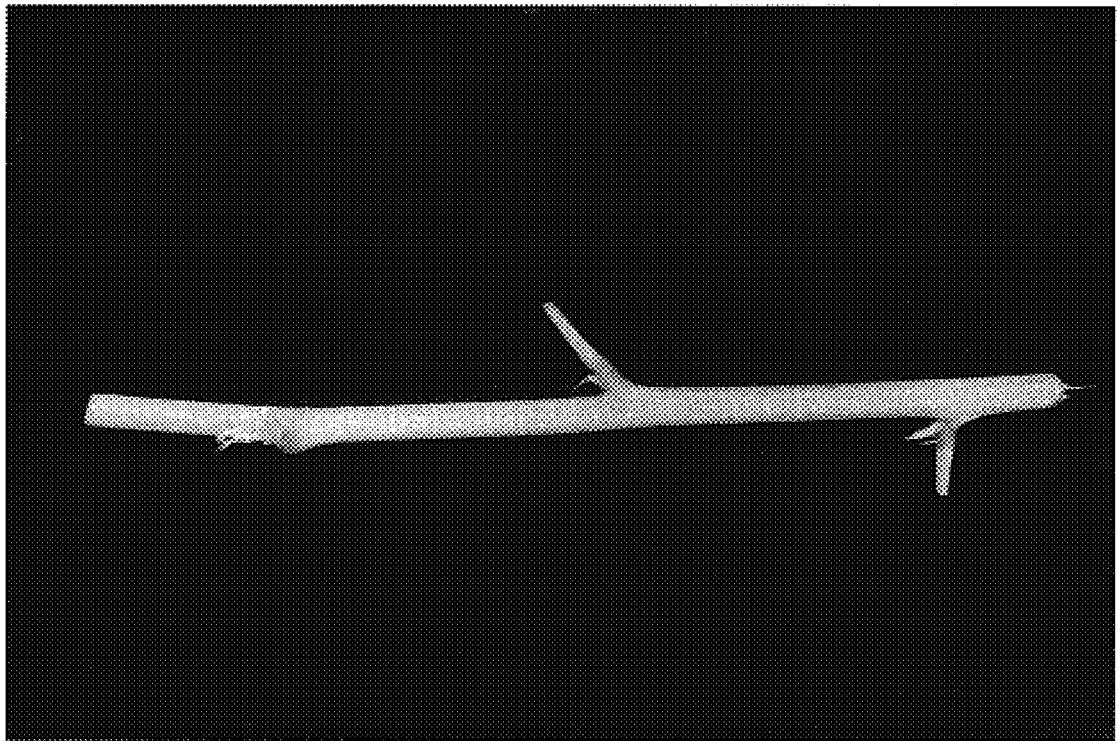
FIG. 3 is a photograph of 'Driscoll Pacifica' primocane shoot.

The following detailed description of the new raspberry cultivar, 'Driscoll Pacifica', is based upon recorded observation of plants and fruit grown between 2003 and 2005 in Watsonville, Calif., and is believed to apply to plants of the 'Driscoll Pacifica' cultivar grown in similar conditions of soil and climate elsewhere.

Throughout this specification, color names beginning with a small letter signify that the name of the color, as used in common speech, is aptly descriptive. Color data beginning with a capital letter and followed by an alphanumeric code indicate the most similar color designations as provided by The Royal Horticultural Society (R.H.S.) Colour Chart published by The Royal Horticultural Society of London, England. Color designations, color descriptions, and other phenotypical descriptions may deviate from the stated values and descriptions depending upon variation in environmental, seasonal, climatic and cultural conditions.

Table 1 provides information on the plant and fruit characteristics of the new raspberry cultivar 'Driscoll Pacifica' compared with characteristics of the unpatented raspberry cultivar 'Heritage'. Observations of the cultivars were taken in comparisons under similar conditions.

The new variety is particularly characterized and distinguished from other cultivars by its fruit firmness, consistent fruit structure and high yield. The fruit color of 'Driscoll Pacifica' is a medium red at harvest and darkens very little after harvest. Fruit of 'Driscoll Pacifica' separates easily from the receptacle and is of excellent firmness at harvest. The fruit of 'Driscoll Pacifica' is consistently large throughout the harvest period.

The primocane and floricane yields of 'Driscoll Pacifica' are high relative to the variety 'Heritage'. 'Driscoll Pacifica' is distinguishable from its pollen parent, selection 'Q471.6', by having better flavored fruit and by having larger fruit from its seed parent, selection 'N234.1'. Additional characteristics of 'Driscoll Pacifica' include an average flower diameter of about 7.9 mm. Additionally, the titratable acidity of 'Driscoll Pacifica' is 1.66 compared to 1.50 for 'Heritage'.

DISEASE ABD STRESS RESISTANCE

Resistance is unknown to powdery mildew and root rots. Cold tolerance of the new cultivar has not been established. Post harvest fruit rot resistance is good in comparison over many selections and varieties.

TABLE 1

PLANT CHARACTERISTICS OF 'DRISCOLL PACIFICA'

| | Driscoll Pacifica | Heritage |
|---|---|---|
| GENERAL | | |
| Plant Size | Med | Large |
| Growth habit | Erect | Erect |
| Productivity | High | Medium |
| Self-fruitfulness | Self-fruitful | Self-Fruitful |
| Time of bud burst | Late | Late |
| Primocane fruiting | | |
| Percent of cane | 40-60 | 20-40 |
| Length flowering as Primocane | | |
| Percent of total yield | 58 | 53 |
| Primocanes | | |
| Number of young shoots | Many | Medium |
| Young shoot pigmentation | Medium | Medium |
| Length (cm) | 173 | 195 |
| Time of shoot emergence | Medium | Medium |
| Glaucosity (waxy bloom) | Absent or weak | Weak |
| Strength | Medium | Medium |
| Cane cross section (from mid cane of primocane) | Rounded to angular | Rounded to angular |
| Dormant cane color | 165-B | 166-B |
| Prickles | | |
| Pigmentation | Green to brown green | Greenish-brown to green |
| Density on young shoots | Sparse | Dense |
| Attitude of tip | Downward | Downward |
| Size | Medium | Medium |
| Size: Length (mm) (base to tip at 1 m height at end of harvest) | 0.8 | 2 |
| Texture | Soft | Heavy |
| Presence and distribution of petioles | Present, regularly distributed | Present, regularly distributed |
| Pubescence on canes | Absent | Absent |
| Internodal distance (cm) (at central ⅓ of cane) | 5.5 | 4.3 |
| LEAVES | | |
| Color | | |
| Face | 147-A | 147-A |

TABLE 1-continued

PLANT CHARACTERISTICS OF 'DRISCOLL PACIFICA'

| | Driscoll Pacifica | Heritage |
|---|---|---|
| Underside | 148-B | 148-C |
| Relief between veins | Medium | Weak |
| Glossiness | Medium | Medium |
| Petiole | | |
| Length (cm) | 5.1 | 7.0 |
| Pigmentation of upper surface | Lightly | Lightly |
| Pigmentation of underside | Unpigmented | Unpigmented |
| Stipule orientation | Clasping | Erect |
| Arrangement | Compound | Compound |
| Number of leaflets | Usually 3 | Sometimes 3, sometimes 5 |
| Overlapping of lateral leaflets | Overlapping | Free to touching |
| Lateral leaflet: length to stalklet (lower pair) | Very short | Very short |
| Terminal leaflet | | |
| Length (cm) | 12.9 | 14.7 |
| Width (cm) | 9.3 | 8.8 |
| Shape | Ovate | Ovate |
| Tip | Acuminate | Acuminate |
| Base | Cordate | Rounded |
| Margin | Doubly serrate | Doubly serrate |
| Lateral leaflets (basal pair) | | |
| Length (cm) | 9.4 | 13.7 |
| Width | 6.6 | 7.8 |
| Orientation | Opposite | Opposite |
| Shape | Ovate | Ovate |
| Tip | Acuminate | Acuminate |
| Base | Rounded | Oblique |
| Margin | Doubly serrate | Doubly serrate |
| Rachis length between terminal leaflet and adjacent lateral leaflet (cm) | 3.4 | 4.6 |
| FLOWERS | | |
| Flowering period | | |
| Primocane | Late May-mid June Through late September | Early July through Early October |
| Floricane | Early April through Mid June | Mid April through Mid June |
| Flower size | Medium | Medium |
| Petal | | |
| Length (cm) | 0.9 | 0.7 |
| Width (cm) | 0.4 | 0.3 |
| Pedicel | | |
| Coloration | Medium | Present, strong Intensity |
| Length | Medium | Short to medium |
| FRUIT | | |
| Harvest Season | | |
| Primocane | Late June-late October | Early August-early November |
| Floricane | Early April-mid July | Late May-mid July |
| Color | Medium Red | Medium Red |
| Immature | 181-B | 180-A |
| Maturing | 184-A | 185-B |
| Mature fruit | 187-A | 185-A |
| Glossiness | Weak | Medium |
| Shape | Ovate | Ovate |
| Dimensions | | |
| Size | Medium | Small |
| Length (mm) | 25 | 19 |
| Width (mm) | 21 | 19 |
| Length:width | 1.2 | 1.0 |

TABLE 1-continued

PLANT CHARACTERISTICS OF 'DRISCOLL PACIFICA'

| | Driscoll Pacifica | Heritage |
|---|---|---|
| Weight (g/Fruit) | | |
| Primocane | 5.0 | 3.4 |
| Floricane | 4.6 | 2.6 |
| Soluble Solids (%) | 10.3 | 10.5 |
| Titratable acidity (% as citric acid) | 1.66 | 1.50 |
| Seeds | | |
| Weight (mg/seed) | 1.42 | 1.62 |
| Number druplets/fruit | 116 | 75 |
| Adherence to plug (1-9) | Medium | Medium |
| Firmness | Med firm to firm | Firm |
| Yield | High | Medium |

What is claimed:

1. A new and distinctive cultivar of raspberry plant, substantially as shown and described.

* * * * *